(12) United States Patent
Han et al.

(10) Patent No.: US 7,713,716 B2
(45) Date of Patent: May 11, 2010

(54) METHOD FOR DETECTING PRESENCE OF TOXIC MATERIAL WITHIN SAMPLE

(75) Inventors: Jung-im Han, Yongin-si (KR); Soo-hyung Choi, Hwaseong-si (KR)

(73) Assignee: Samsung Electronics Co., Ltd. (KR)

( * ) Notice: Subject to any disclaimer, the term of this patent is extended or adjusted under 35 U.S.C. 154(b) by 178 days.

(21) Appl. No.: 11/610,851

(22) Filed: Dec. 14, 2006

(65) Prior Publication Data

US 2007/0148723 A1 Jun. 28, 2007

(30) Foreign Application Priority Data

Dec. 28, 2005 (KR) .................. 10-2005-0131881

(51) Int. Cl.
*C12Q 1/26* (2006.01)
(52) U.S. Cl. ........................................ 435/25
(58) Field of Classification Search .............. 435/25
See application file for complete search history.

(56) References Cited

U.S. PATENT DOCUMENTS

| 4,808,517 | A | | 2/1989 | Blondin et al. | |
|---|---|---|---|---|---|
| 5,843,696 | A | * | 12/1998 | Read et al. | ............... 435/25 |
| 6,099,760 | A | * | 8/2000 | Jameison et al. | ............ 252/700 |
| 2003/0059839 | A1 | * | 3/2003 | Obiso et al. | ............... 435/7.1 |
| 2008/0057559 | A1 | * | 3/2008 | Nacamulli et al. | .......... 435/183 |

FOREIGN PATENT DOCUMENTS

EP 0228290 7/1987

OTHER PUBLICATIONS

Knobeloch, et al.; "Use of Submitochondrial Particles for Prediction of Chemical Toxicity in Man"; Bull. Environ. Contam. Toxicol.; vol. 44; pp. 661-668; 1990.
European Search Report dated May 31, 2007 for Application No. 06120263.6 (All references cited in Search Report are listed above).
Man, F., Omanovic, S. Journal of Electroanalytical Chemistry 2004, 568, 301-313.

* cited by examiner

*Primary Examiner*—Ralph Gitomer
(74) *Attorney, Agent, or Firm*—Cantor Colburn LLP

(57) ABSTRACT

Provided is a method for detecting the degree of toxicity of toxic materials within a sample. The method includes contacting sub-mitochondrial particles having competent mitochondrial enzyme formed from the inner membranes of mitochondria, an electron donor which transmits electrons to the electron transfer system of the sub-mitochondrial particles, and a sample which will be tested; adding tris-2,2'-bipyridyl-ruthenium (II) ion to the reaction mixture; and measuring electrical variables of the reaction mixture. Also, provided is an apparatus and kit for detecting the presence of toxic materials within a sample.

7 Claims, 4 Drawing Sheets

METHOD FOR DETECTING PRESENCE OF TOXIC MATERIAL WITHIN SAMPLE

This application claims priority to Korean Patent Application No. 10-2005-0131881, filed on Dec. 28, 2005, and all the benefits accruing therefrom under 35 U.S.C. § 119, the content of which is incorporated herein by reference in its entirety.

BACKGROUND OF THE INVENTION

1. Field of the Invention

The present invention relates to a method and apparatus for detecting presence of toxic materials within a sample.

2. Description of the Related Art

Use of mitochondria or sub-mitochondrial particles is well known as a biological analysis instrument for detecting the presence of toxic materials within environmental samples. For example, U.S. Pat. No. 4,808,517 discloses (a) suspension of sub-mitochondrial particles having competent mitochondrial enzyme formed from inner membranes of mitochondria, (b) an analysis medium including a substrate in which either a substrate or enzyme reaction product thereof may be detected using a spectroscopic detection method when the analysis medium is transformed by mitochondrial enzymes, and (c) a process of mixing environmental samples in a common vessel. Such a method of analyzing toxic materials within an environmental sample includes determining influences of the sample on enzyme activity within the suspension including sub-mitochondrial particles by measuring the changes in the substrate using spectroscopic measurement.

In U.S. Patent Application Publication No. 2003/0059839, a tris-bipyridyl-ruthenium complex ((Ru(bpy)$_3$(II)) is used to induce electrochemiluminescence ("ECL") by acting as an ECL label. ECL is light emission caused by the response of an electrically stimulated species. Thus, a species which is induced to emit ECL is called an ECL label or an ECL active species.

Conventional methods are mostly used for detecting optical signals. However, methods of analyzing toxic materials by detecting signals other than optical signals are still unknown in the art.

BRIEF SUMMARY OF THE INVENTION

An embodiment of a method according to the present invention provides a method of detecting the presence of toxic materials within a sample.

An embodiment of an apparatus according to the present invention also provides an apparatus for detecting the presence of toxic materials within a sample.

In an exemplary embodiment, a method of detecting the presence of toxic materials within a sample, includes contacting sub-mitochondrial particles having competent mitochondrial enzyme formed from the inner membranes of mitochondria, an electron donor which transmits electrons to the electron transfer system of sub-mitochondrial particles, and a sample to be tested; adding tris-2,2'-bipyridyl-ruthenium (II) (also referred to herein as Ru(bpy)$_3$(II) and as [Ru(bpy)$_3$]$^{2+}$) ion to the reaction mixture; and measuring electrical variables of the reaction mixture.

In another exemplary embodiment of the apparatus, an apparatus for detecting the presence of toxic materials within a sample is provided, where the apparatus includes a reaction vessel and a measuring unit for measuring electrical variables in the reaction vessel. The reaction vessel includes sub-mitochondrial particles having competent mitochondrial enzymes formed from inner membranes of mitochondria, and an electron donor, which may transmit electrons to the electron transfer system of the sub-mitochondrial particles.

In another exemplary embodiment, a kit for electrically analyzing the presence of toxic materials within a sample is provided. The kit includes sub-mitochondrial particles having competent mitochondrial enzymes formed from inner membranes of mitochondria; an electron donor which may transmit electrons to an electron transfer system of sub-mitochondrial particles; and tris-2,2'-bipyridyl-ruthenium (II) ion.

BRIEF DESCRIPTION OF THE DRAWINGS

The above and other features and advantages of the exemplary embodiments according to the present invention will become more apparent by describing in detail exemplary embodiments thereof with reference to the attached drawings in which.

DETAILED DESCRIPTION OF THE INVENTION

Figure 1A:
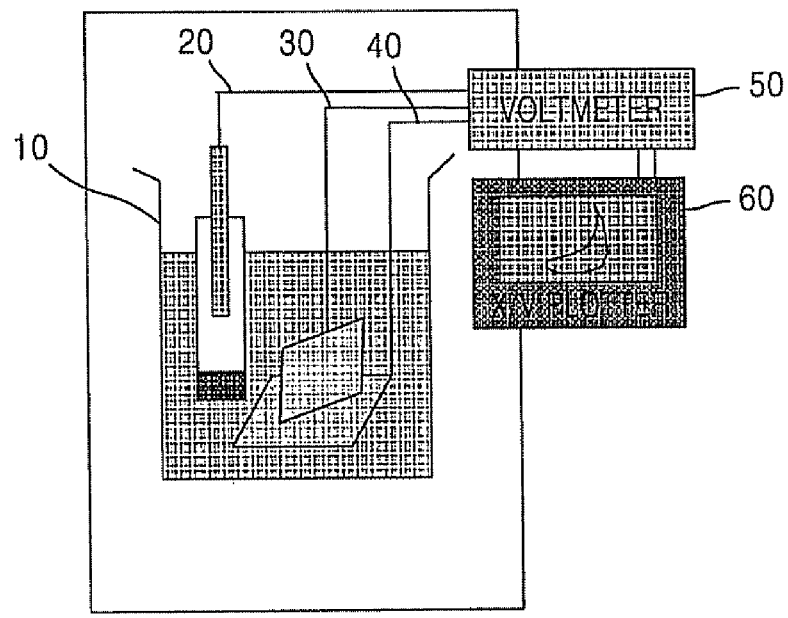
FIG. 1A is a diagram illustrating an exemplary embodiment of a current measuring apparatus according to the present invention.

The invention now will be described more fully hereinafter with reference to the accompanying drawings and examples, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

The terminology used herein is for the purpose of describing particular embodiments only and is not intended to be limiting of the invention. The terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to").

The term "competent enzyme" indicates an enzyme that is active in an mitochondrial electron transfer system.

Embodiments of the invention are described herein with reference to cross-section illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In an embodiment, a method of detecting the presence of toxic materials within a sample includes contacting sub-mitochondrial particles having competent mitochondrial enzyme formed from inner membranes of mitochondria, an electron donor which transmits electrons to the electron transfer system of sub-mitochondrial particles, and a sample which will be tested.

The sub-mitochondrial particles ("SMP") include a lipid bilayer membrane vesicle obtained by micelle formation from a fraction of a cristae membranes when mitochondria are ruptured. That is, whole mitochondria derived from any origin may be ruptured by ultrasonic waves, a detergent, such as a digitonin, or a French press. Membrane fractions can be separated from cytoplasmic residue by a centrifugal separation. The membrane segments are then allowed to transform into vesicles, which model the behavior of intact inner membranes of mitochondria.

Such sub-mitochondrial particles can model the behaviors of mitochondria and a large amount of sub-mitochondrial particles also can be saved by being frozen or lyophilized after manufacturing. Thus, an aliquot of a sub-mitochondrial particle product can be relatively easily used in performing a toxicant assay, which can require an extended time period.

The sub-mitochondrial particles may be manufactured by sonicating whole mitochondria so that cristae membranes of the mitochondria transform into micelles.

Exemplary embodiments of the sub-mitochondrial particles can be manufactured using a conventional method or can be purchased commercially.

For example, a method of manufacturing the sub-mitochondrial particles is disclosed in U.S. Pat. No. 4,808,517. Firstly, in order to manufacture the sub-mitochondrial particles, whole mitochondria are prepared. Mitochondria derived from any origin may be used. The sub-mitochondrial particles may be manufactured from fresh mitochondria or from frozen mitochondria. Once the sub-mitochondrial particles are manufactured, the sub-mitochondrial particles can be stored in a preserved mixture at −20° C. Also, for storage purposes, the sub-mitochondrial particles can be lyophilized. In order to use the exemplary embodiments of lyophilized sub-mitochondrial particles, they can simply be defrosted. Lyophilized product can be saturated with an analyzing medium before use and thus can be relatively simply transformed.

The sub-mitochondrial particles include competent mitochondrial enzyme. As used herein, the term "competent mitochondrial enzyme", means that the enzyme involved in the electron transfer system of mitochondria is active. Accordingly, the method measures the extent of the effects of toxic materials on the electron transfer system of mitochondria or on the electron transfer system of sub-mitochondrial particles by changing the effects to an electric signal. Specifically, toxic materials affect the enzyme of the electron transfer system of sub-mitochondrial particles, and thus, affect the amount of electrons transmitted from an electron donor to the electron transfer system of the mitochondria. Consequently, toxic materials affect the amount of electron donors within a reaction solution. The method thus includes electrically measuring the amount of electron donors within a reaction solution and thereby measures influences on the electron transfer system, including the extent of toxicity. However, the application of the method should not be considered as limited to the effect of toxic materials.

The mitochondrial enzyme may consist of NADH-dehydrogenase, coenzyme-Q-cytochrome C reductase, and cytochrome C oxidase.

The electron donor may include at least one selected from the group consisting of NADH and NADPH.

The toxic materials may include any toxic materials, which has an influence on the mitochondrial and/or sub-mitochondrial particle electron transfer systems. Exemplary toxic materials include, but are not limited to, ethanol, methanol, phenols, heavy metals, and solvents.

The method of contacting described above can be performed under any condition, including for example a physiological condition or a condition similar to a physiological condition, as long as the enzymes of the electron transfer system can react in that condition. Contacting may thus be performed in a solution having physiological salt and ionic strength of a pH of about 7, such as for example in a phosphate buffered saline (PBS solution), or in another buffer, for a predetermined time. When the contacting is performed under the physiological condition or in a solution similar to such physiological condition, the amount of the sub-mitochondrial particles may be, but is not limited to, 0.1 to 0.5 mg/ml and the amount of the electron donors may be 1 to 30 mM. As the concentration of the sub-mitochondrial particles and the electron donors increase, the reaction speeds also increase accordingly. Thus, the sub-mitochondrial particles and the electron donors may be used by considering the desired reaction speed and appropriately adjusting the concentration.

In addition, in an embodiment, a method of detecting the presence of toxic materials within a sample includes adding tris-2,2'-bipyridyl-ruthenium (II) (i.e., Ru(bpy)$_3$(II)), also [Ru(bpy)$_3$]$^{2+}$) to the reaction mixture. Compounds of the tris-2,2'-bipyridyl-ruthenium (II) ion can be purchased commercially, and may be used at a total concentration of 1 to 5 mM. Since the desired electrical property of tris-2,2'-bipyridyl-ruthenium (II) ion can vary according to the concentration of the electron donors, the tris-2,2'-bipyridyl-ruthenium (II) ion is added to measure electrical variables according to the concentration of the electron donor. When voltage is applied, the Ru(bpy)$_3$(II)) ion is converted reversibly to + bivalent or + trivalent intermediate by an oxidation-reduction reaction. For example, the extent of reversible oxidation-reduction can change according to the concentration of NADH and the electrical signal of the solution including the Ru(bpy)$_3$(II) ion. For example, the current value at a specific voltage changes linearly according to the concentration of NADH.

In an embodiment of the method of detecting the presence of toxic materials within a sample, the method includes measuring electrical variables of the reaction mixture. The electrical variables may include at least one selected from the group consisting of current, voltage, impedance, and capacitance.

In an embodiment, the electrical variables include one of a cathode peak current and an anode peak current as determined using a cyclic voltammogram (obtained using cyclic voltammetry). The electrical variables may be measured within a potential (i.e., voltage) range in which an oxidized electron donor, such as NAD+ or NDAP+, is not reduced. The current can be measured in a potential range of 0.85 to 1.35 V. When the electrical variables to be measured include current (i.e., amperage) at a specific voltage, the measured current value increases with increasing concentration of a sample containing a compound to be tested, when compared with that of a control sample, in which the tested compound is not included and the current value does not increase. In this way, it can be determined that toxic compounds (and hence toxicity) are present in the sample.

In another embodiment, an apparatus for detecting the presence of toxic materials within a sample includes a reaction vessel and a measuring unit for measuring electrical variables included in the reaction vessel. The reaction vessel includes sub-mitochondrial particles having competent mitochondrial enzyme formed from inner membranes of mitochondria and an electron donor, which transmits electrons to the electron transfer system of the sub-mitochondrial particles.

The reaction vessel may further include a sample, which will be tested.

The reaction vessel may further include tris-2,2'-bipyridyl-ruthenium (II) ion.

The sub-mitochondrial particles may be manufactured by sonicating whole mitochondria so that cristae membranes of the mitochondria transform into micelles. The mitochondrial enzymes may include at least one enzyme selected from the group consisting of NADH-dehydrogenase, coenzyme-Q-cytochrome C reductase, and cytochrome C oxidase.

The electron donor may include at least one selected from the group consisting of NADH and NADPH.

The description of the sub-mitochondrial particles, the competent enzymes, the electron donors, the toxic materials, and tris-2,2'-bipyridyl-ruthenium (II) ion of the apparatus are as described for the method.

In an embodiment, the reaction vessel disclosed herein can be made of any useful material and can be of any shape, as long as the vessel can contain sub-mitochondrial particles, electron donors, toxic materials, and tris-2,2'-bipyridyl-ruthenium (II) ion, and includes equipment for measuring electrical variables.

The measuring unit of the electric variables may include at least one selected from the group consisting of voltage, current, resistance, and impedance.

The reaction vessel may include a working electrode, to which a voltmeter (i.e., a potentiostat) is electrically connected, a counter electrode, and a standard electrode (such as, for example, an Ag/AgCl electrode).

In another embodiment, a kit for electrically analyzing the presence of toxic materials within a sample includes sub-mitochondrial particles having competent mitochondrial enzyme formed from the inner membranes of mitochondria, an electron donor which transmits electrons to the electron transfer system of the sub-mitochondrial particles, and tris-2,2'-bipyridyl-ruthenium (II) ion.

The sub-mitochondrial particles may be manufactured by sonicating whole mitochondria so that cristae membranes of the mitochondria transform into micelles.

The sub-mitochondrial particles may be frozen or lyophilized.

The mitochondrial enzyme may include at least one enzyme selected from the group consisting of NADH-dehydrogenase, coenzyme-Q-cytochrome C reductase, and cytochrome C oxidase.

The electron donor may include at least one selected from the group consisting of NADH and NADPH.

In an embodiment, in the kit, the sub-mitochondrial particles, the competent enzymes, the electron donors, toxic materials, and tris-2,2'-bipyridyl-ruthenium (II) ion are each as described in the method disclosed herein.

The present invention will be described in greater detail with reference to the following examples. The following examples are for illustrative purposes and are not intended to limit the scope of the invention.

EXAMPLES

Structure of Current Measuring Apparatus Using a Cyclic Voltammetry Method and Range of Applied Voltage.

(1) Current Measuring Apparatus Using a Cyclic Voltammetry Method

Figure 1B:
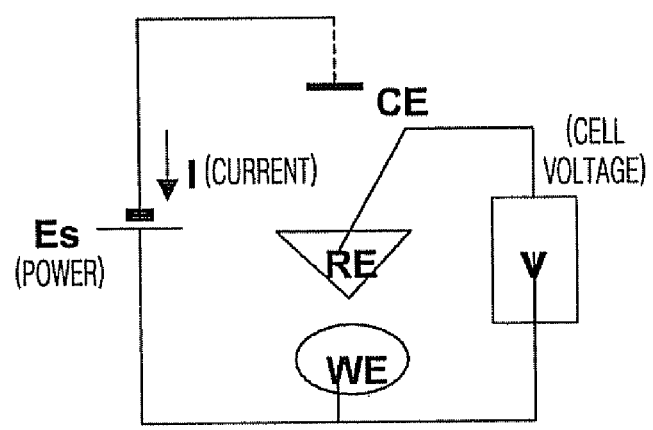
FIG. 1B is a schematic diagram illustrating an exemplary embodiment of the current measuring apparatus.

FIGS. 1A is a diagram of an exemplary embodiment of a current measuring device; and FIG. 1B is a schematic diagram of an exemplary embodiment of a current measuring apparatus. Referring to FIG. 1A, a reaction vessel 10 includes an Ag/AgCl standard electrode 20 (RE in FIG. 1B), a platinum working electrode 30 (WE in FIG. 1B), and a platinum counter electrode 40 (CE in FIG. 1B). The standard electrode 20, the working electrode 30, and the counter electrode 40 are connected to a voltmeter 50 (e.g., a Perkin-Elmer VMP multichannel potentiostat; V in FIG. 1B). An X/Y plotter 60 is connected to the voltmeter 50.

In an Example, an experiment was conducted by adding a 6 millimolar (mM) solution of reduced nicotinamide adenine dinucleotide (NADH) in 0.5× phosphate-buffered saline (PBS) into a reaction vessel and measuring a current range with a scan speed of 50 mV/sec cyclic voltammogram (CV) and 7 milliliters (ml) of a measuring solution.

(2) Range of Applied Voltage

In order to measure a peak current using a cyclic voltammetry method, voltage may be in a range where oxidized electron donors may not be reduced a second time (after an initial reduction). Accordingly, the measurement voltage is selected such that NAD+ or NADP+, an oxidized form of electron donor used in the Example, is not reduced to NADPH.

Figure 2:
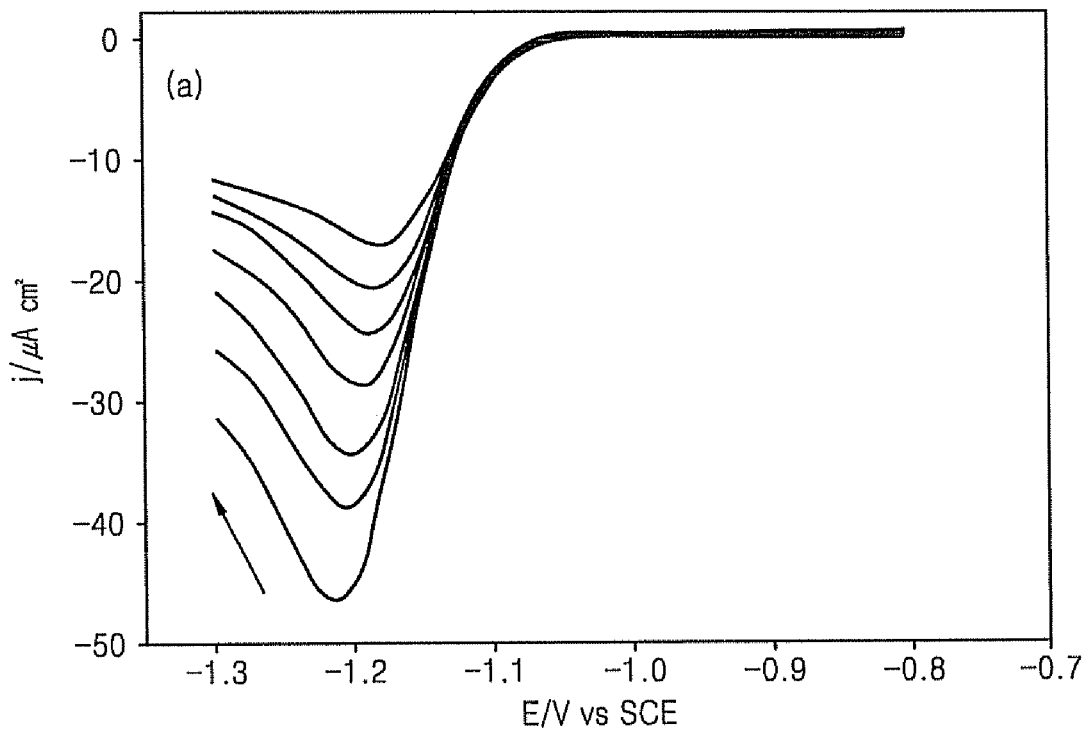
FIG. 2 is a current density-voltage graph of a 7.25 millimolar (mM) nicotinamide adenine dinucleotide ("NADH") solution (See *Journal of Electroanalytical Chemistry* 2004, 568, 301-313, FIG. 3.)

FIG. 2 is a conventional current density-voltage graph of a 7.25 mM NADH solution (*Journal of Electroanalytical Chemistry* 2004, 568, 301-313). In FIG. 2, it can be seen that NAD+ is not reduced to NADH in the range of 0.85 to 1.35 V/Ag/AgCl. In the Examples described below, peak current was measured in the range of 0.85 to 1.35 V/Ag/AgCl.

Example 1

Detecting Toxicity of Ethanol and Sorbitol According to an Exemplary Embodiment of the Method The cathode peak current was measured using the current measuring apparatus illustrated in FIG. 1A, in accordance with the concentration of ethanol as a toxic material, and sorbitol as a non-toxic material against a cell.

Figure 3:
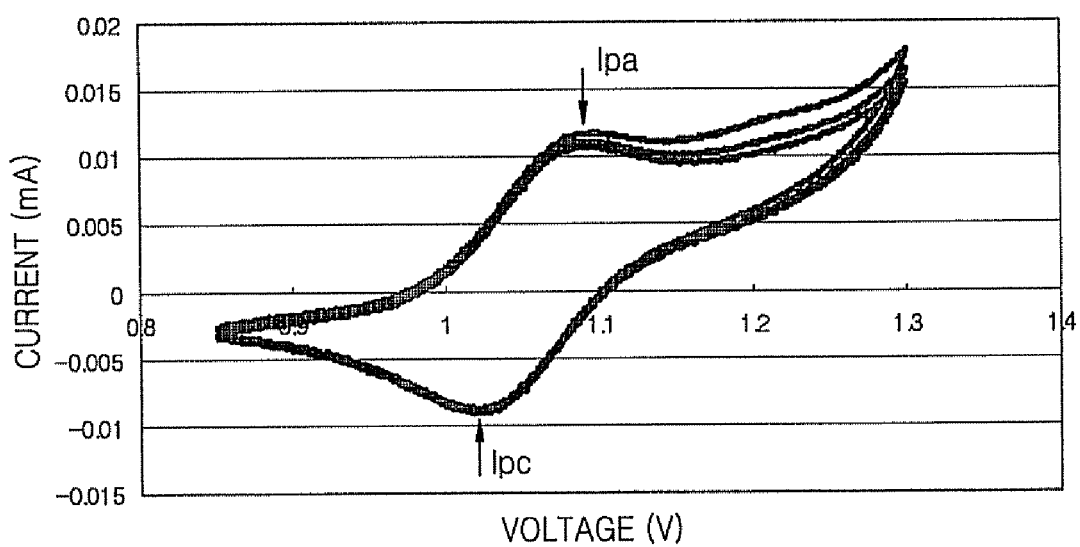
FIG. 3 is a graph showing a cyclic voltammogram of 2.5 mM Ru(bpy)$_3$$^{2+}$ in phosphate-buffered saline ("PBS")

0.5×PBS including 0.5 mg/ml of SMP (submitochondrial particle) (Havard Bioscience), 6 mM of NADH, and 50 mM of KCl was allowed to react at ambient temperature for 1 hour. Then the reaction solution and 5 mM Ru(bpy)$_3^{2+}$ which exists in 0.5×PBS were mixed in a ratio of 1:1 to obtain a cyclic voltammogram using a voltmeter (potentiostat), thereby obtaining a cathode peak current. The cyclic voltammogram was measured with a scan speed of 50 mV/sec CV at a sweep range of 0.85 to 1.35 V. Subsequently, in the cyclic voltammogram of 2.5 mM Ru(bpy)$_3^{2+}$ in which toxic materials are not included, voltage generated at the cathode peak current and the anode peak current was 1.019 V and 1.2 V, respectively. FIG. 3 is a graph showing the cyclic voltammogram of 2.5 mM Ru(bpy)$_3^{2+}$ in phosphate-buffered saline (PBS).

Then, ethanol samples having final concentrations (on a weight basis) of 0 wt %, 2.5 wt %, 5 wt %, and 10 wt %, or a sample having 2.5 wt % of sorbitol was added to 0.5×PBS including 0.5 mg/ml of SMP, (submitochondrial particle), 6 mM of NADH, and 50 mM of KCl to prepare 7 ml of a final reaction solution and was allowed to react for 1 hour at ambient temperature.

Next, absorbance of the final reaction solution was measured at 340 nanometers (nm) using a spectrophotometer and the concentration of NADH was measured using an optical method. In addition, the reaction solution and 5 mM Ru(bpy)$_3^{2+}$ in 0.5×PBS were mixed in a ratio of 1:1 and a cathode peak current at 1.019 volts (V) was obtained using a voltmeter (potentiostat). The cyclic voltammogram was measured with a scan speed of 50 mV/sec CV at a sweep range of 0.85 to 1.35V.

Figure 4:
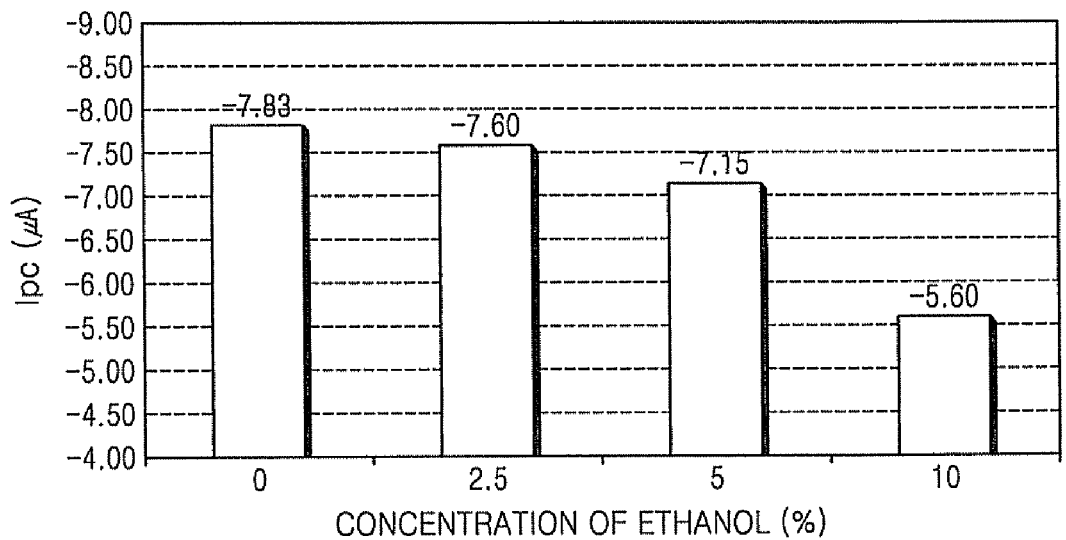
FIG. 4 is a graph illustrating a cathode peak current at 1.019 volts (V) in a cyclic voltammogram with respect to concentration of ethanol.

FIG. 4 is a graph illustrating a cathode peak current at 1.019V in a cyclic voltammogram at various concentration levels of ethanol. FIG. 4 shows that as the concentration of ethanol increases, the cathode peak current correspondingly moves towards in less negative (i.e., more positive, cathodic) direction. Such movement shows that ethanol obstructs the electron transfer reaction of sub-mitochondrial particles, and that a cell contains toxic materials. In addition, for a solution of ethanol with a concentration of 2.5 wt %, which is considered in the art as a concentration containing a relatively small amount of toxic material, the cathode peak current moves toward a less negative value (i.e., trends in a positive direction) relative to a sample having an ethanol concentration of 0 wt %. This result shows the high sensitivity of the electrical measuring method disclosed herein.

Figure 5:
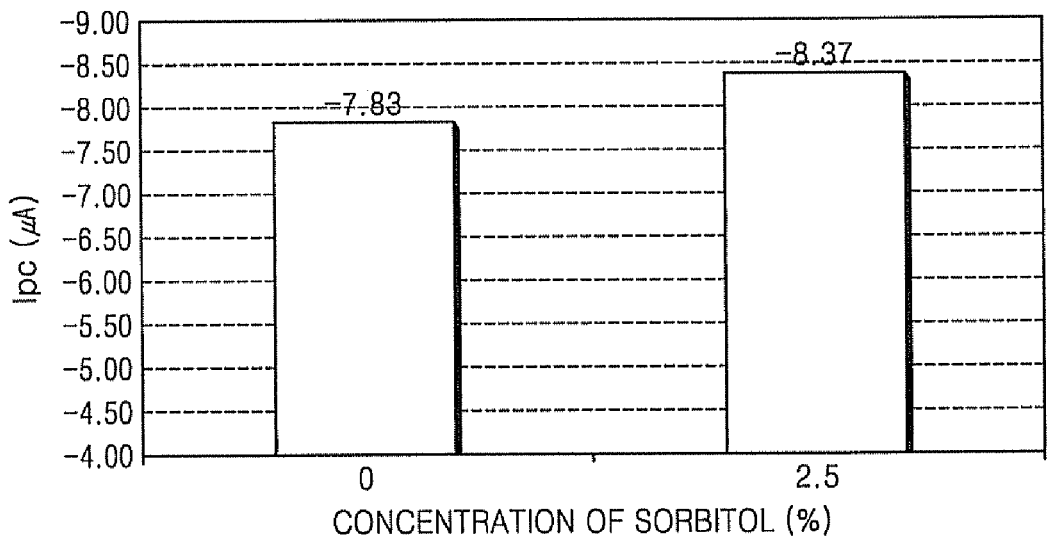
FIG. 5 is a graph illustrating a cathode peak current at 1.019 V in a cyclic voltammogram with respect to concentration of sorbitol.

FIG. 5 is a graph illustrating the cathode peak current at 1.019 V in a cyclic voltammogram with respect to concentration of sorbitol. Referring to FIG. 5, when the concentration of sorbitol is 2.5 wt %, the cathode peak current moves towards a more negative value (i.e., trends in a negative direction) when compared with a sample having a concentration of sorbitol of 0 wt %. This shows that sorbitol does not include toxic material but slightly changes an electrical property of the solution that includes the 5 mM Ru(bpy)$_3^{2+}$. Optical measurements taken at an absorbance at 340 nm using a spectrophotometer, of a sample with a sorbitol concentration of 2.5 wt %, shows no changes when compared to the absorbance of a sample with a sorbitol concentration of 0 wt %, thereby showing the sorbitol sample has no toxicity (data is not illustrated herein).

Example 2

Relationship Between the Method Shown in Exemplary Embodiments and a Conventional Optical Method for Detecting Toxic Materials Applying the method described in Example 1, a cathode peak current at 1.019V with respect to a concentration of ethanol was measured. A concentration of NADH was also measured by measuring absorbance at 340 nm using a spectrophotometer. Subsequently, a relationship between the value of a cathode peak current and a concentration of NADH measured using an optical method was identified.

Figure 6:
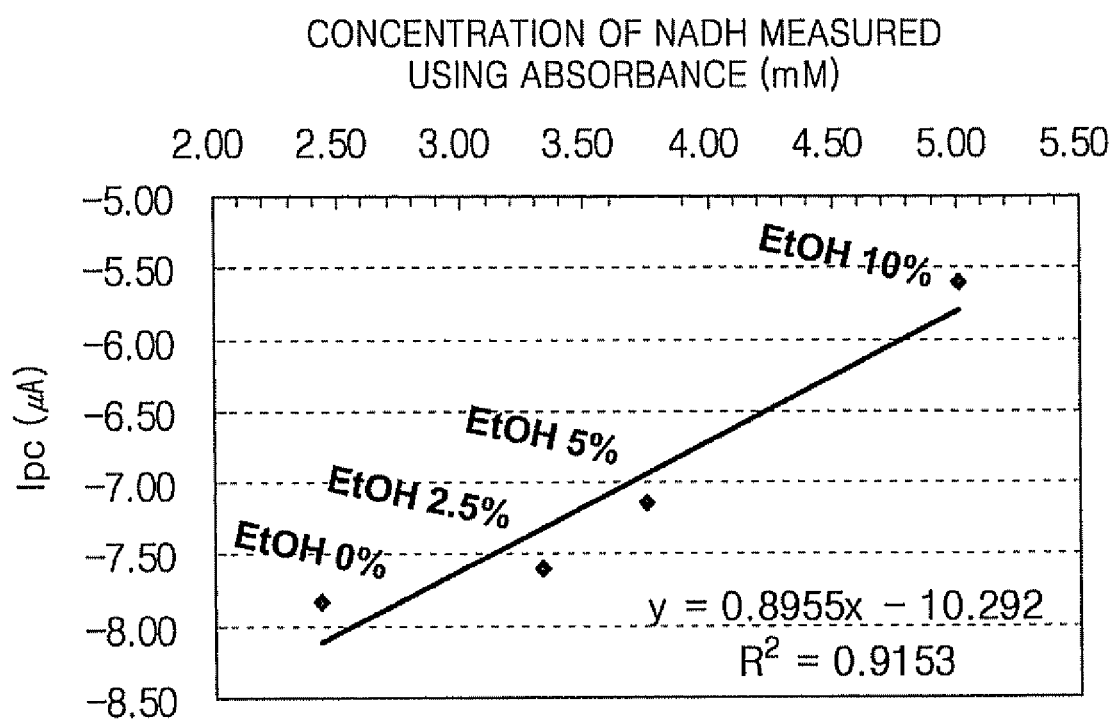
FIG. 6 is a graph illustrating a relationship between the value of a cathode peak current measured electrically and NADH concentration measured optically.

FIG. 6 is a graph illustrating a relationship between the value of a cathode peak current measured electrically and a NADH concentration measured optically. FIG. 6 shows that the value of the cathode peak current based on the electrical measurement and the NADH concentrations based on the optical measurement correlate with each other.

According to an embodiment of the method of detecting the presence of toxic materials within a sample according to the present invention, toxicity of a compound can be detected with high sensitivity under a condition similar to a physiological condition.

According to an embodiment of the apparatus for detecting the presence of toxic materials within a sample described according to the present invention, toxicity of a compound within a sample can be relatively easily detected and the apparatus can be relatively easily miniaturized.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of detecting the presence of toxic materials within a sample, the method comprising:
   contacting
      sub-mitochondrial particles comprising cristae membranes having a competent mitochondrial enzyme formed from the inner membranes of mitochondria,
      an electron donor which transmits electrons to an electron transfer system of the sub-mitochondrial particles, and
      the sample;
   adding tris-2,2'-bipyridyl-ruthenium (II) ion to form a reaction mixture;
   measuring the amount of electron donor by an electrical variable of the reaction mixture, and
   determining the presence of the toxic materials in the sample by an increase of the electrical variable compared to that of a control sample in which the toxic materials are not included,
   wherein the toxic material affects the amount of electron donor within the reaction mixture, and
   wherein the toxic materials are selected from the group consisting of ethanol, methanol, and phenol.

2. The method of claim 1, wherein the sub-mitochondrial particles are manufactured by sonicating whole mitochondria so that cristae membranes of the mitochondria transform into micelles.

3. The method of claim 1, wherein the competent mitochondrial enzyme consists of NADH-dehydrogenase, coenzyme-Q-cytochrome C reductase and cytochrome C oxidase.

4. The method of claim 1, wherein the electron donor comprises at least one selected from the group consisting of NADH and NADPH.

5. The method of claim 1, wherein the electrical variable comprises at least one selected from the group consisting of current, voltage, impedance, and capacitance.

6. The method of claim 1, wherein the electrical variable is cathode peak current or anode peak cuffent, as determined by cyclic voltammetry.

7. The method of claim 6, wherein the cathode peak current or anode peak current is measured at a voltage of 0.85 V to 1.35 V.

* * * * *